United States Patent [19]

Shroot et al.

[11] Patent Number: 4,889,865
[45] Date of Patent: Dec. 26, 1989

[54] 10-ARYL-1,8-DIHYDROXY-9- ANTHRONES AND THEIR ESTERS

[76] Inventors: Braham Shroot, Villa 35, Hameaux de Val-Bosquet, Chemin de Val-Bosquet, Antibes 06600; Gérard Lang, 44, avenue Lacour, 95210 Saint Gratien; Jean Maignan, 8, rue Halévy, 93290 Tremblay les Gonesse; Serge Restlé, 140, rue Anatole France, 93600 Aulnay-sous-Bois; Christopher Hensby, 89, Chemin d'Andon, Villa Madru, 06410 Biot; Michel Colin, 10, Allée Cécile, 93190 Livry-Gargan, all of France

[21] Appl. No.: 312,945

[22] Filed: Feb. 21, 1989

Related U.S. Application Data

[60] Division of Ser. No. 176,974, Apr. 4, 1988, Pat. No. 4,843,097, which is a continuation-in-part of Ser. No. 744,240, Jun. 13, 1985, abandoned, and a continuation-in-part of Ser. No. 940,068, Dec. 10, 1986, abandoned.

[30] Foreign Application Priority Data

Jun. 13, 1984 [FR] France .............................. 84 09203
Dec. 11, 1985 [FR] France .............................. 85 18338

[51] Int. Cl.⁴ ........................ A61K 31/12; A61K 7/13
[52] U.S. Cl. .................................. 514/332; 514/333; 514/335; 514/336; 514/340; 514/342; 514/344; 514/345; 514/346; 514/349; 514/350; 514/351; 514/352; 514/355; 514/356; 514/357; 514/365; 514/374; 514/438; 514/444; 514/445; 514/447; 514/448; 546/255; 546/256; 546/261; 546/262; 546/263; 546/264; 546/265; 546/266; 546/267; 546/275; 546/277; 546/280; 546/281; 546/284; 546/285; 546/286; 546/287; 546/288; 546/289; 546/290; 546/293; 546/297; 546/299; 546/300; 546/301; 546/302; 546/304; 546/309; 546/310; 546/311; 546/312; 546/329; 546/330; 546/334; 546/335; 546/336; 546/337; 546/338; 546/339; 546/340; 546/344; 546/345; 546/346; 546/348; 548/146; 548/189; 548/237; 548/238; 549/59; 549/60; 549/61; 549/62; 549/63; 549/64; 549/65; 549/66; 549/68; 549/69; 549/70; 549/71; 549/72; 549/73; 549/74; 549/75; 549/76; 549/77; 549/78; 549/79; 549/80; 549/81

[58] Field of Search ....................... 549/59, 60, 61, 62, 549/63, 64, 65, 66, 68, 69, 70, 71, 72, 73, 74, 75, 76, 77, 78, 79, 80, 81; 546/255, 256, 268, 275, 280, 261, 262, 263, 265, 266, 267, 281, 284, 285, 286, 287, 288, 289, 290, 293, 297, 298, 300, 301, 302, 304, 309, 310, 311, 312, 329, 330, 334, 335, 336, 337, 338, 339, 340, 344, 345, 346, 348; 548/146, 189, 237, 238; 514/332, 333, 335, 336, 340, 342, 344, 346, 349, 350, 351, 352, 355, 356, 357, 365, 374, 438, 444, 445, 447, 448

[56] References Cited

U.S. PATENT DOCUMENTS

| 2,292,306 | 8/1942 | Vittam et al. | 260/351 |
| 2,841,597 | 7/1958 | Clar et al. | 260/351 |
| 3,519,655 | 7/1970 | Ryan et al. | 260/351 |
| 4,299,846 | 11/1981 | Mustakallio et al. | 260/351 |
| 4,327,114 | 4/1982 | Brickl et al. | 260/351 |
| 4,464,301 | 8/1984 | Shroot et al. | 260/351 |
| 4,568,743 | 2/1986 | Shroot et al. | 260/351 |
| 4,677,123 | 7/1987 | Shroot et al. | 514/680 |

*Primary Examiner*—Richard L. Raymond
*Assistant Examiner*—Raymond Covington
*Attorney, Agent, or Firm*—Roger M. Rickert

[57] ABSTRACT

Mono, di and tri-esters of 1,8-dihydroxy-10-phenyl-9-anthrone or -9-anthranol have the formula

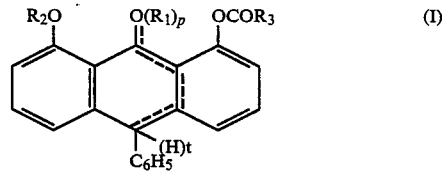

wherein
p is 0 or 1,
(a) when p=0, t=1 and $R_2$ represents hydrogen or —$COR_3$,
(b) when p=1, t=0 and $R_1$ and $R_2$ each independently represent hydrogen or —$COR_3$,
$R_3$ represents linear or branched alkyl having 1–17 carbon atoms, cycloalkyl, phenyl or phenyl substituted by lower alkyl, lower alkoxy, halogen, a nitro function, —$CF_3$ or a hydroxyl function, and mixtures of said esters. These esters are prepared by reacting 1,8-dihydroxy-10-phenyl-9-anthrone with an activated form of an acid. The esters are useful in human or veterinary medicine and in cosmetic compositions.

3 Claims, No Drawings

10-ARYL-1,8-DIHYDROXY-9- ANTHRONES AND THEIR ESTERS

This is a division of application Ser. No. 176,974, filed Apr. 4, 1988, now U.S. Pat. No. 4,843,097 which is a continuation-in-part of applications Ser. No. 744,240 filed June 13, 1985 and Ser. No. 940,068 filed Dec. 10, 1986, both abandoned.

The present invention relates to new derivatives of 1,8-dihydroxy-9 anthrone or anthraline, particularly to derivatives substituted in the 10 position by an aromatic radical and to mono-, di-, and triesters of 10-aryl-1,8 dihydroxy 9-anthrones. The present invention also relates to the process for preparing these compounds, and to their use in human and veterinary medicine and in cosmetics. The new derivatives of the present invention as well as the esters are particularly useful as anti-proliferative agents, in the treatment of cancerous tumors, psoriasis, and warts, and as anti-inflammatory agents in the treatment of rheumatic disorders, dermatoses, eczema, seborrheic and pellicular dermatitis, and sunburn. In cosmetic compositions, these compounds are useful as anti-acne, anti-dandruff, and anti-seborrheic agents, and are useful in combatting hair loss.

The 10-aryl, 1,8-dihydroxy-9-anthrones of the present invention can be represented by the following general formula:

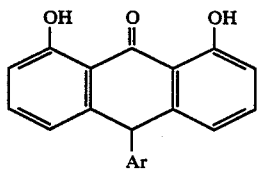
(I)

wherein Ar represents an aromatic radical corresponding to one of the following formulas:

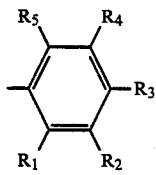
(i)

wherein $R_1$, $R_2$, $R_3$, $R_4$, and $R_5$ each independently represent hydrogen, halogen, —$CF_3$, hydroxy, lower alkoxy, lower cycloalkyl, lower hydroxyalkyl, lower alkoxy, nitrile,

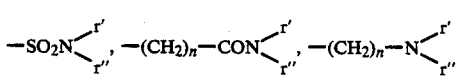

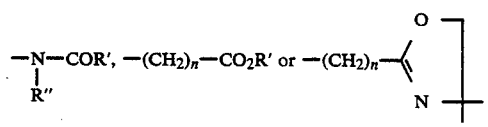

wherein r' and r'' each independently represent hydrogen or lower alkyl; n is 0 is a whole number ranging from 1 to 3 inclusive; and R' and R'' represent hydrogen, linear or branched lower alkyl, or aryl optionally substituted, with the proviso that at least one of $R_1$–$R_5$ is other than a hydrogen atom,

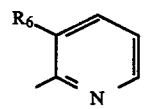
(ii)

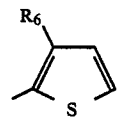
(iii)

wherein $R_6$ represents one of the meanings given for $R_1$ through $R_5$, above and

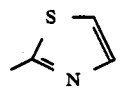
(iv)

When $R_1$–$R_5$ represent halogen, the said halogen is preferably fluorine or chlorine.

By "lower alkyl" is meant an alkyl having 1 to 6 carbon atoms, preferably methyl, ethyl, propyl, isopropyl, butyl, isobutyl, t-butyl, pentyl, isopentyl, or hexyl.

By "lower alkoxy" is meant an alkoxy having 1 to 4 carbon atoms, particularly methoxy, ethoxy, propoxy, or isopropoxy.

By "lower cycloalkyl" is meant cyclopropyl, cyclobutyl, cyclopentyl, or cyclohexyl.

By "lower hydroxyalkyl" is meant one wherein the alkyl moiety has 1 to 3 carbon atoms; particularly hydroxymethyl, 2-hydroxy ethyl, or 2,3-dihydroxy-propyl.

When in the compounds of formula (I), Ar represents an aromatic residue of the formula:

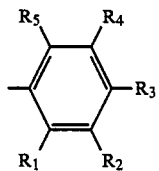

the preferred compounds are those in which:
(1) $R_1$ (or $R_5$) represents lower alkoxy or a radical of the formula

wherein R' represents linear or branched alkyl having 1 to 5 carbon atoms and R'' represents hydrogen; $R_3$ represents hydrogen or lower alkoxy; and $R_2$, $R_4$, and $R_5$ (or $R_1$) represent hydrogen.
(2) $R_2$ (or $R_4$) represents —$CF_3$, lower alkoxy, or hydroxyl; and $R_5$ represent hydrogen; and
(3) $R_3$ represents lower alkoxy, and $R_1$, $R_2$, $R_4$, and $R_5$ represent hydrogen.

In a preferred embodiment, $R_6$ represents hydrogen.
Representative compounds of formula (I) include the following:
1,8-dihydroxy-10-[(2'',2''-N-dimethylpropanoyl) 2'-amino phenyl]-anthrone, 1,8-dihydroxy-10-(2',4'-dimethoxy-phenyl)-anthrone,
1,8-dihydroxy-10-(4'-methoxy-phenyl)-anthrone,
1,8-dihydroxy-10-(3'-trifluoromethyl)-anthrone,
1,8-dihydroxy-10-(3'-methoxy-phenyl)-anthrone,
1,8-dihydroxy-10-(3'-hydroxy phenyl)-anthrone,
1,8-dihydroxy-10-(2'-methoxy phenyl)-anthrone,
1,8-dihydroxy-10-(2-thienyl)-anthrone and
1,8-dihydroxy-10-(2-thiazolyl)-anthrone.

The mono-, di-, and triesters of 10-Aryl-1,8 dihydroxy 9-anthrones can be represented by the following formula:

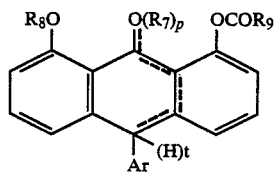

wherein
p is 0 or 1
(a) when p=0, t=1 and $R_8$ represents hydrogen or —$COR_9$,
(b) when p=1, t=0 and $R_7$ and $R_8$ each independently represent hydrogen or —$COR_9$,
$R_9$ represents linear or branched alkyl having 1–17 carbon atoms, cycloalkyl, phenyl, phenyl substituted by lower alkyl, lower alkoxy, halogen, nitro, —$CF_3$ or hydroxyl, and
Ar represents an aromatic radical corresponding to one of the following formulas:

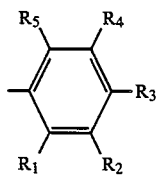

wherein $R_1$, $R_2$, $R_3$, $R_4$, and $R_5$ each independently represent hydrogen, halogen, —$CF_3$, hydroxy, lower alkyl, lower cycloalkyl, lower hydroxyalkyl, lower alkoxy, nitrile,

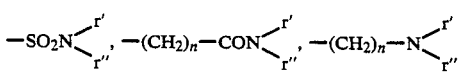

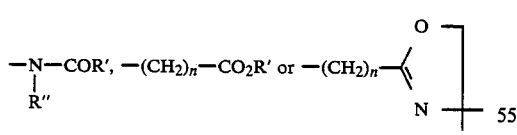

wherein r' and r" each independently represent hydrogen or lower alkyl; n is 0 or a whole number ranging from 1 to 3 inclusive; and R' and R" represent hydrogen, linear or branched lower alkyl, or aryl optionally substituted,

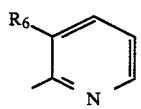

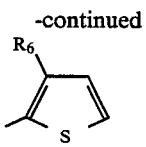

wherein $R_6$ represents one of the meanings given for $R_1$ through $R_5$, above and

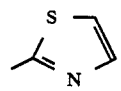

Representative linear or branched alkyl having 1 to 17 carbon atoms includes for instance methyl, ethyl, propyl, isopropyl, butyl, isobutyl, t-butyl, pentyl, isopentyl, heptyl, nonyl, and decyl radicals.

When $R_9$ represents cycloalkyl, it is a cyclopropyl, cyclobutyl, cyclopentyl, or cyclohexyl radical.

When the phenyl radical is substituted by alkyl, the said alkyl moiety is preferably methyl, ethyl, or t-butyl.

When the phenyl radical is substituted by alkoxy, the said alkoxy moiety is preferably methoxy or ethoxy.

When the phenyl radical is substituted by halogen, the said halogen is preferably chlorine or fluorine.

In accordance with a preferred embodiment of the present invention, the compounds are di-esters or tri-esters having the following formulas:

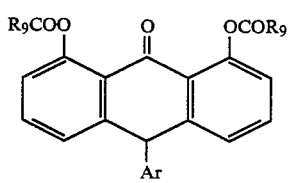

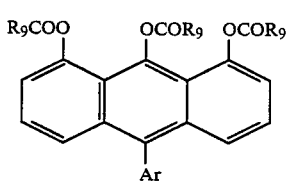

wherein:
$R_9$ is elected from the group consisting of linear or branched alkyl having 1–17 carbon atoms, cyclopentyl, cyclohexyl, phenyl and phenyl substituted by lower alkyl, lower alkoxy, halogen nitro, —$CF_3$ and hydroxyl, and
Ar is selected from

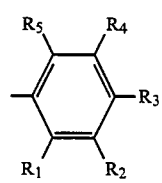

wherein:
(a) $R_1$ (or $R_5$) represents hydrogen, lower alkoxy or a radical of the formula:

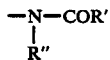

wherein R' represents linear or branched alkyl having 1 to 5 carbon atoms and R" represents hydrogen; $R_3$ represents hydrogen or lower alkoxy: and $R_2$, $R_4$ and $R_5$ (or $R_1$)represent hydrogen (b) $R_2$ (or $R_4$) represents —$CF_3$, lower alkoxy, or hydroxyl; and $R_1$, $R_2$, $R_4$ (or $R_2$) and $R_5$ represent hydrogen, and (c) $R_3$ represents lower alkoxy and $R_1$, $R_2$, $R_4$ and $R_5$ represent hydrogen.

and (ii)

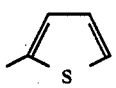

Representative esters according to the invention of formula (II) include, particularly, the following:
10-phenyl-1,8,9-triacetoxy anthracene,
10-phenyl-1,8,9-tripropionyloxy anthracene,
10-phenyl-1,8,9-tributyryloxy anthracene,
10-phenyl-1,8,9-triisobutyryloxy anthracene,
1,8-diisobutyryloxy-10-phenyl-9-anthrone,
10-phenyl-1,8,9-tricyclohexylcarbonyloxy anthracene
1,8-dipivaloyloxy-10-phenyl-9-anthrone,
10-phenyl-1,8,9-tribenzoyloxy anthracene,
10-phenyl-1,8,9-tricyclopentylcarbonyloxy anthracene,
10-phenyl-1,8,9-trioctanoyloxy anthracene,
10-phenyl-1,8,9-triundecanoyloxy anthracene,
10-phenyl-1,8,9-trioctadecanoyloxy anthracene,
10-phenyl-1,8,9-tritolylcarbonyloxy anthracene,
10-phenyl-1,8,9-tri(p-methoxybenzoyloxy) anthracene,
10-phenyl-1,8,9-tri[m-(trifluoromethyl) benzoyloxy] anthracene,
10-(3'-methoxy phenyl)-1,8,9-triacetoxy-anthracene,
10-(3'-methoxy phenyl)-1,8,9-tripropanoyloxy anthracene,
10-(2-thienyl)-1,8,9-triacetoxy anthracene,
10-(2-thienyl)-1,8,9-tripropanoyloxy-anthracene and
1,8-dipivaloyloxy-10-(2-thienyl) anthrone.

The compounds of formula (I) of the present invention can be obtained in two steps starting with 1,8-dihydroxy anthracene, in accordance with the following reaction scheme:

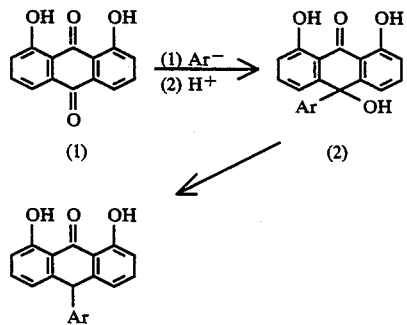

The first step comprises reacting an aromatic carbanion with 1,8-dihydroxy anthraquinone (1), which leads, after acidification, to the compound formula (2).

The second step comprises reducing the intermediate compound (2) in the presence of metallic tin or stannous chloride, which leads to the compound of formula (I) of the present invention.

The reaction with the aromatic carbanion can be accomplished using an organolithium or organomagnesium compound.

The aromatic organolithium compounds may be obtained by two different methods:

The first method comprises reacting butyl lithium, or a complex thereof with tetramethylethylene diamine, with an aromatic compound, whose substituent(s) activate the carbon on which it is desired to effect metallation.

Methods described by D. W. Slocum et al, J.O.C., p. 3653, 1976, or by V. Snieckus et al, J.O.C., 44, P. 4803, 1979, can be employed.

The second method for producing the aromatic lithium compounds comprises treating an aromatic halogen derivative, principally, a brominated derivative, with butyl lithium according to methods described by P. Beak, et al., Acc. Chem. Res., P. 306, 1982, and by W. E. Parham, et al, Acc. Chem. Res., P. 300, 1982.

When it is desired to obtain the aromatic carbanion from a magnesium compound, the preceding method is repeated using an aromatic halogen derivative which is transformed into magnesium compounds, in accordance with conventional procedures, in an anhydrous solvent, such as tetrahydrofuran or ether.

A process comprising reacting an aromatic lithium compound with 1,8-dihydroxy anthraquinone is particularly preferred because, unlike aromatic magnesium compounds, this lithium process leads to selective addition on the carbonyl at the 10-position of the anthraquinone ring. This is not the case when using aromatic magnesium compounds, where addition at the 9-position can, in some cases, be observed.

It has also been noted that by using a considerable excess of aromatic lithium compound, at least 4 molar equivalents greater than the quantity of 1,8-dihydroxyanthraquinone, it is not necessary, as in known processes, to protect hydroxyl functional groups in position 1 or 8 in order to obtain the aromatic derivatives in the 10-position of the anthrone ring.

The addition reaction of aromatic lithium compound on the 1,8-dihydroxy-anthraquinone is generally carried out in an anhydrous solvent medium such as ethyl ether or tetrahydrofuran, at a temperature between $-80°$ C. and $0°$ C., by addition of the aromatic lithium compound in the ether or tetrahydrofuran to a solution in the same solvent of the 1,8-dihydroxy anthraquinone.

After the addition, the reaction mixture is continuously stirred at the same temperature for a period of time ranging from 30 minutes to 2 hours. The end of the reaction is determined by the absence of 1,8-dihydroxy anthraquinone in thin-layer chromatography.

The reaction mixture is then acidified at the ambient temperature and the organic phase is then washed with water and dried on anhydrous magnesium sulfate.

Following evaporation of the solvent, the intermediate compound (2) or 10-aryl-1,8,10-trihydroxy anthrone, is purified by recrystallization or chromatography on silica gel.

When the reaction is carried out starting with an aromatic magnesium compound, the reaction conditions are similar to those used starting with an aromatic lithium compound. However, after addition, the mixture is permited to return to ambient temperature and stirring is continued for several hours, optionally under solvent reflux, until the disappearance of the 1,8-dihydroxy anthraquinone as measured by thin-layer chromatography.

The second stage of the process of the present invention comprises reducing the 10-aryl-1,8,10-trihydroxy anthrone (2) in order to obtain compounds of the present invention having formula (I). This reduction reaction is carried out in an acetic acid medium in the presence of stannous chloride or metallic tin and concentrated hydrochloric acid.

The reaction is generally carried out at ambient temperature for a period of time ranging from between one-half to 5 hours, the end of the reaction being determined by the absence of the initial reactant in thin-layer chromatography.

If the reaction is not complete, the reaction mixture can be placed in a water bath.

When the temperature of the reaction mixture returns to ambient temperature the reaction mixture is poured into water, which causes the precipitation of the expected product which is then purified by recrystallization in an appropriate solvent.

The present invention also relates to a process for preparing the mono, di and tri-esters of 1,8-dihydroxy-10-aryl-9-anthrones as defined above by formula (II)

The 1,8-dihydroxy-10-aryl-9-anthrones, having three possible sites for O-acylation which, depending on the operational conditions and the nature of the reactant, permit the production of mono, di or tri-esters.

These esters can, however, be obtained in the form of a mixture that can be fractionated by chromatography.

These esters according to the present invention are obtained by reacting the 1,8-dihydroxy-10-aryl-9-anthrones, with an activated form of an acid such as an acid anhydride, or an acid chloride, in presence of a base and preferably an aromatic amine such as pyridine, optionally in an aromatic solvent such as toluene and at a temperature between 20° and 130° C.

The formation of mono, di or tri-esters is a function of the molar amounts of acid anhydride or acid chloride reacted and of the reaction time.

For the preparation of mono and di-esters there are employed, preferably, 1.5 to 2.5 equivalents of an acid chloride or acid anhydride. The reaction is followed or monitored by thin layer chromatography in order to terminate the reation either at the mono-ester stage or at the di-ester stage.

For the preparation of tri-esters a large excess of acid chloride or acid anhydride is employed and in order to complete the reaction, the reaction temperature is preferably 80°–110° C.

When there is employed a particularly encumbered acid chloride such as, for example, pivaloyl chloride, it is particularly easy to produce di-esters even in the presence of an excess without noticing a significant formation of the corresponding tri-ester.

Where an acid chloride, which is easily eliminated either by evaporation or by washing in a basic medium, is employed it is desirable to effect the reaction by using the acid chloride both as the solvent and as the reactant and by adding from 4 to 8 equivalents of pyridine.

In this case, the reaction is carried out at a temperature between 20° and 60° C. This reaction is particularly rapid.

After the end of the reaction, when it is carried out in a solvent, the reaction medium is poured into water and the various washings are effected using, principally, a solution of sodium bicarbonate. The organic phase is then dried on magnesium sulfate and filtered. The resulting product can be purified by recrystallization, or by chromatography on silica gel by using, preferably, toluene or a toluene/ethyl acetate mixture as the eluant.

The present invention also relates to pharmaceutical and cosmetic compositions characterized by the fact that they contain, as the active component, at least one compound of formula I or II.

In these compositions, the concentration of the active component generally varies from 0.005 to 70% by weight, depending on the method by which it is administered, but preferably the concentration varies from 0.05 to 10% by weight.

These compositions can also contain inert or pharmacodynamically active additives, such as binding agents, fillers; diluents, thickeners, preservatives, etc.

Orally administered compositions can also contain flavoring agents.

Topically applied compositions can be provided in the form of salves, ointments, cremes, gels, tinctures, solutions, lotions, sprays, suspensions, micropowders, or shampoos.

In accordance with this embodiment of the present invention, 1 to 5 g of a composition containing from 0.01 to 5 g of the active component per 100 g of the composition are applied in one or two applications to the areas of skin to be treated.

Compositions administered enterally or parenterally can be provided in the form of tablets, granules, gels, capsules, syrups, drinkable suspensions, ingestable powders in packets, or injectable solutions or suspensions.

Enteral or parenteral dosages are generally administered in quantities of 0.05 to 5 g of active component per day for adults, taken at one time or in several doses.

Tests have shown that the compounds of the present invention exhibit good activity when incorporated in various pharmaceutical or cosmetic vehicles.

Several non-limiting examples of the preparation of the compounds of the present invention are given to illustrate the present invention as well as several examples of compositions for therapeutic and cosmetic uses are given, as well as several examples of composition for therapeutic and cosmetic use are given.

EXAMPLE 1

Preparation of
1,8-dihydroxy-10-[(2″,2″-N-dimethyl-propanoyl)-2-amino phenyl] anthrone (a) To 18 g of N-pivaloyl aniline in 100 cm³ of anhydrous tetrahydrofuran (THF) there are added 100 cm³ of n-butyl-lithium (2.5M) under an inert atmosphere at 0.C.

After addition, the reaction mixture is left for 24 hours at ambient temperature. One then adds, slowly at 0° C., a solution of 5 g of 1,8-dihydroxy anthraquinone in 100 cm³ of anhydrous tetrahydrofuran (THF).

The resulting mixture is stirred for 4 hours at ambient temperature, and then acidified with 75 cm³ of acetic acid. This acidified mixture is then poured into 500 cm³ of water and is extracted with dichloromethane. The organic phase is dried on magnesium sulfate and concentrated under reduced pressure. The expected product is purified by silica gel chromatography. The product thus obtained is 1 g of yellow crystals of 10-[2″, 2″-N-dimethyl propanoyl) 2′-amino phenyl]1,8,10-trihydroxy anthrone having a melting point of 257°–259° C.

The NMR spectrum conforms of the structure of the expected product.

Elemental analysis: $C_{25}H_{23}O_5N$; Calculated: C 71.92; H 5.55; O 19.16; N 3.35; Found: 71.71; H 5.56 O 18.92 N 3.43.

(b) To a suspension of 250 mg of 10-[(2″, 2″-N-dimethyl propanoyl)2′-amino phenyl]1,8,10-trihydroxy anthrone, obtained above in (a) in 25 cm³ of glacial acetic acid, there are added under an inert atmosphere 400 mg of stannous chloride and several drops of concentrated hydrochloric acid.

The reaction mixture is then stirred for 2 hours at ambient temperature. The reaction mixture is then poured into 100 cm³ of water. The expected product precipitates and is then filtered and dried. This product is then taken up in 50 cm³ of dichloromethane and the mixture is then stirred in the presence of 2 g of silica. The solution is filtered, then concentrated under reduced pressure. The expected product is precipitated by addition of hexane, filtered and dried, yielding 100 mg of yellow crystals having a melting point of 176°–177° C.

The NMR spectrum conforms to the structure of the expected product, as does the mass spectrum, m/e 401.

EXAMPLE 2

Preparation of 1,8-dihydroxy-10-(2′,2′-dimethoxy phenyl) anthrone (a) To a solution of 22.1 g of 1,3-dimethoxy benzene in solution in 50 cm³ of anhydrous ethyl ether, there are added 100 cm³ of n-butyl-lithium (1.6M) at ambient temperature and under an argon atmosphere. After 24 hours, this solution is quickly added to a suspension of 5 g of 1,8-dihydroxy anthraquinone in 150 cm³ of anhydrous THF at a temperature of −78° C. Upon completion of the reaction, the reaction mixture is acidified using 50 cm³ of glacial acetic acid. After washing with water (200 cm³) and drying on magnesium sulfate, the organic phase is concentrated under reduced pressure, then purified by silica gel chromatography, yielding 200 mg of yellow powder of 10-(2′4′-dimethoxy phenyl)-1,8,10-trihydroxy anthrone having a melting point of 207° C.

The NMR'H 250 MHz spectrum conforms to the structure of the expected product.

Elemental analysis: $C_{22}H_{18}O_6$; Calculated: C 69.85; H 4.79; Found: C 70.54; H 4.85.

(b) To a solution of 100 g of 10-(2′,4′-dimethoxy phenyl)-1,8,10-trihydroxy anthrone, such as obtained in (a) above, in 25 cm³ of glacial acetic acid, there are added, under an inert atmosphere, 200 mg of stannous chloride and several drops of concentrated hydrochloric acid. The resulting reaction mixture is stirred for 5 hours at ambient temperature and then poured into 100 cm³ of water, so as to precipitate the expected product which is then filtered and dried, yielding 50 mg of a cream-colored powder having a melting point of 152° C.

Mass spectrum m/e: 362.

EXAMPLE 3

Preparation of 1,8-dihydroxy-10-(4′-methoxy phenyl) anthrone)

(a) To a solution of 28 g of para-bromanisole in 50 cm³ of anhydrous THF there are added 100 cm³ of n-butyl-lithium (1.6M) under an argon atmosphere at −78° C. The solution is left to return to ambient temperature for one hour. It is then decanted into a dropping funnel to which is added a suspension of 7.2 g of 1,8 dihydroxy anthraquinone in 300 cm³ of anhydrous THF under an argon atmosphere at a temperature of −78° C. At the end of the addition, the reaction mixture is permitted to return to ambient temperature for 24 hours. The reaction mixture is then acidified with 50 cm³ of glacial acetic acid and poured into 500 cm³ of water.

After extraction using dichloromethane, the organic phase is dried on magnesium sulfate and concentrated under reduced pressure.

There are thus obtained, after silica gel chromatography 3.4 g of the expected product. After recrystallization in a toluene-hexane mixture, there are obtained yellow crystals of 10-(4′-methoxy phenyl)-1,8,10-trihydroxy anthrone having a melting point of 172°–173° C.

The NMR spectrum conforms to the structure of the expected product.

Elemental analysis: $C_{21}H_{16}O_5$; Calculated: C 72.40; H 4.63; O 22.97; Found: C 72.47; H 4.61; O 22.87.

(b) To a suspension of 200 mg of 10-(4′-methoxy phenyl)-1,8,10-trihydroxy anthrone, such as obtained in (a) above, in 10 cm³ of glacial acetic acid, there are added 200 mg of stannous chloride and a few drops of concentrated hydrochloric acid. The resulting mixture is stirred for two hours under an inert atmosphere. The expected product is obtained by precipitation from the reaction mixture in 100 cm³ of water, yielding 150 mg of greenish-yellow powder that decomposes starting at 215° C.

The NMR spectrum and mass spectrum (m/e=332) conform to the structure of the expected product.

Elemental analysis: $C_{21}H_{16}O_4$ Calculated: C 75.89; H 4.85; O 19.25; Found: C 75.78; H 4.80; O 19.26.

EXAMPLE 4

Preparation of 1,8-dihydroxy-10-(3′-trifluoromethyl phenyl) anthrone (a) To a solution of 25 g of 3-trifluoromethyl bromobenzene in 100 ml of anhydrous THF there are added 100 cm³ of n-butyl-lithium (1.6M) under an argon atmosphere at −78° C.

After the addition, the reaction mixture is permitted to return to ambient temperature.

The resulting solution is then added, slowly, under an inert atmosphere to a suspension of 7.2 g of 1,8-dihydroxy anthraquinone in 200 cm³ of anhydrous THF at −78° C.

The reaction mixture is maintained at this temperature for 1 hour and then brought back to ambient temperature. The reaction mixture is then then acidified by the addition of 50 cm³ of glacial acetic acid. The reaction mixture is washed with 200 cm³ of water, dried, concentrated, and then purified on a silica gel column. 1.2 g of the expected product are isolated and then recrystallized in a toluene-hexane mixture, yielding yellow crystals of 10-(3′-trifluoromethyl phenyl)-1,8,10-trihydroxy anthrone having a melting point of 222°–223° C.

The NMR 'H MHz spectrum conforms to the structure of the expected product.

Elemental analysis: $C_{21}H_{13}F_3O_4$; Calculated: C 65,30; H 3.33; Found: C 64,95; H 3.35.

(b) To a solution of 150 mg of 10-(3′-trifluoromethyl phenyl)-1,8,10-trihydroxy anthrone, such obtained in (a) above, in 25 cm³ of glacial acetic acid placed under a nitrogen atmosphere, there are added 200 mg of stannous chloride and several drops of concentrated hydrochloric acid. The reaction mixture is stirred for 3 hours at ambient temperature, following which the expected product is precipitated by adding of 100 cm³ of water. The product is filtered and dried, yielding 50 mg of a yellow powder having a melting point of 210°–211° C.

Mass spectrum: m/e: 370.

EXAMPLE 5

Preparation of 1,8-dihydroxy-10-(3'-methoxy phenyl) anthrone (a) Method using organomagnesium compounds To 2.7 g of magnesium in 40 cm³ of anhydrous THF, there are added, under a nitrogen atmosphere, 20.8 g of m-bromoanisole under reflux of the THF. The reflux is maintained for 1 hour after the addition is complete. The reaction mixture is then added slowly to a suspension of 5 g of 1,8-dihydroxy anthraquinone in 60 cm³ of anhydrous THF under a nitrogen atmosphere at 0° C. The reaction mixture is left over night at ambient temperature and then heated for 8 hours at 50° C.

The reaction mixture is then acidified by the addition of 9 cm³ of glacial acetic acid, after which 150 cm³ of water are added. The product is extracted with ethylether (100 cm³), after which the organic phase is dried and concentrated under vacuum. The reaction mixture is then purified using silica gel chromatography, yielding 1.2 g of 10-(3'-methoxy phenyl)-1,8,10-trihydroxy anthrone.

The NMR spectrum as well as the mass spectrum m/e=348) conform to the structure of the expected product.

(a') Method using organolithium compounds

To a solution of 28 g of m-bromoanisole in 50 cm³ of anhydrous THF there added, under an argon atmosphere at −78° C., 100 cm³ of n-butyl-lithium (1.6M). The resulting reaction solution is left to return ambient temperature for one hour. The solution obtained is then decanted into a dropping funnel to which is added a suspension of 7.2 g of 1,8-dihydroxy anthraquinone in 300 cm³ of anhydrous THF under argon atmosphere at −78° C. After addition, the reaction mixture is left to return to ambient temperature for 24 hours. It is then acidified with 50 cm³ of glacial acetic acid, and then washed with 500 cm³ of water. The organic phase is separated, then dried on magnesium sulfate and concentrated under reduced pressure. The expected product is crystallized by the addition of toluene. 4.2 g of 10-(3'-methoxy phenyl)-1,8,10-trihydroxy anthrone having a melting point of 202° C. are isolated.

The NMR spectrum conforms to the structure of the expected product.

Elemental analysis: $C_{21}H_{16}O_5$; Calculated: C 72.40; H4.63; O 22.97; Found: C 72.73; H4.61; O 22.62.

(b) to a solution of 3 g of 10-(3'-methoxy phenyl)-1,8,10-trihydroxy anthrone such as obtained above in (a) or (a'), in about 100 cm³ of glacial acetic acid, placed under an inert atmosphere, there are added 3 g of stannous chloride, then 3 cm³ of concentrated hydrochloric acid. The reaction mixture is then stirred for 2 hours at ambient temperature, after which the expected product is precipitated by the addition of 500 cm³ of water. After drying, 2.7 g of a yellow powder having a melting point of 187° C. are obtained.

The NMR spectrum conforms to the structure of the expected product.

Elemental analysis: $C_{21}H_{16}O_4$; Calculated: C 75.89; H 4.85; O 19.25; Found: C 75.71; H 4.92; O 19.24.

EXAMPLE 6

Preparation of 1,8-dihydroxy-10-(3'-hydroxy phenyl) anthrone 500 mg of 1,8-dihydroxy-10-(3'-methoxy-phenyl) anthrone, such as that obtained in example 5, are added to a solution of 35 cm³ of hydrobromic acid under an inert atmosphere. The resulting mixture is heated to 100°–110° C. and the progress of the reaction is followed by thin-layer chromatography. Following the total disappearance of the initial reactant, the solution is poured into about 200 cm³ of water. The resulting precipitate is filtered. After drying, the product is dissolved in 150 cm³ of dichloromethane, then stirred in the presence of 3 g of silica. The solution is filtered and then concetrated under reduced pressure. The expected product crystallizes by the addition of hexane, yielding 310 mg of yellow crystals having a melting point of 204° C.

The NMR spectrum conforms to the structure of the expected product.

Elemental analysis: $C_{20}H_{14}O_4$; Calculated: C 75.46; H 4.43; O 20.11; Found: C 75.57; H 4.37; O 19.96.

EXAMPLE 7

Preparation of 1,8-dihydroxy-10-(2'-methoxy phenyl) anthrone (a) To 2.55 g of magnesium in 15 cm³ of anhydrous THF, there are added under a nitrogen atmosphere, 16.2 g of o-bromoanisole at reflux of the THF. The reflux is maintained for one-half hour completion of the addition. The solution obtained is then slowly added to a suspension of 5 g of 1,8-dihydroxy anthraquinone in 50 cm³ of anhydrous THF under a nitrogen atmosphere at 0° C. The reaction mixture is left over night at ambient temperature, at which point it is acidified with 9 cm³ of glacial acetic acid, to which are added 150 cm³ of water.

The organic phase is decanted, washed twice with water (100 cm³), then dried on magnesium sulfate. The solution is then concentrated under a vacuum and then taken up with toluene. The solution is filtered, and by the addition of hexane there are obtained 5 g of a yellow precipitate, which is recrystallized in a toluene-hexane mixture. The resulting light yellow crystals of 10-(2'methoxy phenyl)-1,8,10-trihydroxy-anthrone have a melting point of 220°–221° C.

Elemental analysis: $C_{21}H_{16}O_5$; Calculated: C 72.40; H 4.63; O 22.97; Found: C 72.59; H 4.65; O 23.21.

(b) To a solution of 2.8 of 10-(2'-methoxy phenyl)-1,8,10-trihydroxy anthrone, such as obtained in (a) above, in 90 cm³ of glacial acetic acid, placed in an inert atmosphere, there are added 4.9 g of stannous chloride, then 14.5 cm³ of concentrated hydrochloric acid. The reaction mixture is then stirred at ambient temperature for 3 hours. The expected product is precipitated by pouring the reaction mixture into 200 cm³ of water. There is thus obtained 1 g of product purified after silica gel chromatography. The yellow crystals thus obtained have a melting point of 191° C.

The NMR spectrum as well as the mass spectrum (m/e=332) conform to the structure of the expected product.

Elemental analysis: $C_{21}H_{16}O_4$; Calculated: C 75.89; H 4.85; O 19.25; Found: C 75.96; H 4.92; O 19.30.

EXAMPLE 8

Preparation of 1,8-dihydroxy-10-(2-thienyl) anthrone (a) To a solution of 12.7 cm$^3$ of thiophene in 100 cm$^3$ of anhydrous ethyl ether there are added 100 cm$^3$ of n-butyl-lithium (1.6M) at 0° C. under an argon atmosphere. After the addition, the solution is maintained at 0° C. for 1 hour and then permitted to return to ambient temperature.

The resulting solution is then slowly added to a suspension of 9.2 g of 1,8-dihydroxy-anthraquinone in 1000 cm$^3$ of anhydrous THF under an argon atmosphere at −78° C. The reaction mixture is permitted to return to ambient temperature, following which it is acidified with 50 cm$^3$ of glacial acetic acid.

The solution is concentrated under reduced pressure, then taken up with ethyl ether. The brown precipitate formed is then filtered and taken up in 100 cm$^3$ of warm methanol, producing yellow crystals of 10-(2-thienyl)-1,8,10-trihydroxy anthrone having a melting point of 191°–192° C.

Elemental analysis: $C_{18}H_{12}O_4S$; Calculated: C 66.65; H 3.73; O 9.89; Found: C 66.20; H 3.66; O 9.10.

(b) To a solution of 5 g of 10-(2-thienyl)-1,8,10-trihydroxy anthrone, such as obtained in (a) above, in 100 cm$^3$ of acetic acid, there are added under an inert atmosphere, 14.6 g of stannous chloride and 20 cm$^3$ of concentrated hydrochloric acid. The resulting mixture is stirred for two hours at ambient temperature and then poured into 200 cm$^3$ of water. The product is filtered and dried, isolating 4.55 g of 1,8-dihydroxy-10-(2-thienyl)-anthrone. After recrystallization in toluene, this substance has a melting point of 181°–182° C.

The NMR spectrum and the mass spectrum (m/e=308) correspond to the structure of the expected product.

Elemental analysis: $C_{18}H_{12}O_3S$; Calculated: C 70.11; H 3.92; O 15.57; S 10.40; Found: C 69.75; H 3.80; O 15.54; S 9.98.

EXAMPLE 9

Preparation of 1,8-dihydroxy-10-(2-thiazolyl) anthrone (a) To a solution of 100 cm$^3$ of n-butyl-lithium (1.5M) in 100 cm$^3$ of anhydrous ethyl ether there are slowly added at −40° C., under an inert atmosphere, 24.6 g of 2-bromo thiazole. After the addition, the temperature of the reaction mixture is adjusted to −78° C. and there are added 9.6, g of 1,8-dihydroxy-anthraquinone dissolved in 1000 cm$^3$ of THF. The reaction medium is then left at ambient temperature for 48 hours, after which it is acidified with 50 cm$^3$ of acetic acid and then poured into 1000 cm$^3$ of water.

The organic phase is dried on magnesium sulfate and then concentrated under reduced pressure. The expected product is purified by silica gel chromatography, thus isolating 3.5 g of 10-(2-thiazalyl)-1,8,10-trihydroxy anthrone provided in the form of a yellow solid that is recrystallized in a toluene-hexane mixture. The crystals have a melting point of 223°–225° C.

The NMR spectrum as well as the mass spectrum (m/e=325) conform to the structure of the expected product.

Elemental analysis: $C_{17}H_{11}NO_4S$; Calculated: C 62.76; H 3.41; O 19.67; N 4.30; S 9.86; Found: C 62.85; H 3.41; O 19.63; N 4.39; S 9.66.

(b) To a suspension of 2 g of 10-(2-thiazolyl)-1,8,10-trihydroxy anthrone such as obtained in (a) above, in 75 cm$^3$ of acetic acid, there are added 2 g of metallic tin and 25 cm$^3$ of hydrochloric acid. The resulting mixture is heated in a water bath for 1 hour, during which time the initial product passes completely into solution. The solution is poured into 200 cm$^3$ of water. The resulting product is filtered, yielding 1 g of 1,8-dihydroxy-10-(2-thiazolyl) anthrone which is recrystallized in methanol. The melting point of the recrystallized product is 142° C.

Elemental analysis: $C_{17}H_{11}NO_3S$ Calculated: C 66.00; H 3.58; N 4.52; O 15.51; S 10.35; Found: C 66.15; H 3.60; N 4.60; O 15.92; S 10.15.

EXAMPLE 10

Preparation of 10-phenyl-1,8,9-triacetoxy anthracene (1) Preparation of 1,8-dihydroxy-10-phenyl-9 anthrone (a) Preparation of 10-phenyl, 1,8,10-trihydroxy-9-anthrone.

In a 2 liter reactor fitted with a mechanical stirrer, an argon lead in tube, a condenser and an introduction funnel, there are placed 30 g of 1,8-dihydroxy anthraquinone and 2 liters of anhydrous tetrahydrofuran. The resulting solution is then cooled to −70° C.

At this temperature, the anthraquinone crystallizes. There is then added, with stirring, over a 30 minute period, a solution which contains 4 equivalents of phenyllithium.

This temperature is maintained throughout the addition between −60° C. and −70° C. At the end of the addition, one ascertains, on a withdrawn sample, that all the 1,8-dihydroxy anthraquinone has been transformed. At this temperature, the reaction mixture is acidified by adding 400 cm$^3$ of acetic acid and it is then permitted to return to ambient temperature. The solvent is evaporated to dryness under reduced pressure and the resulting product, in the form of an oily mass, crystallizes on stirring in water.

The resulting crystals are filtered, washed with dichloromethane and then dried, yielding 32 g of yellow crystals which are recrystallized in methanol. The product has a melting point of 216° C.

Analysis: $C_{20}H_{14}O_4$; Calculated: C-75.46; N-4.43 O-20.10; Found: C-75.48; N-4.35 O-19.95.

(b) Preparation of 1,8-dihydroxy-10-phenyl-9-anthrone.

In a 2 liter reactor fitted with a mechanical stirrer and an argon lead-in tube, there are introduced 50 g of 10-phenyl-1,8,10-trihydroxy-9-anthrone, 200 g of crushed stannous chloride and 2 liters of acetic acid.

To this mixture, stirred at ambient temperature, there are slowly added, over a 30-minute period, 200 cm$^3$ of concentrated HCl. The disappearance of the 10-phenyl-1,8,10-trihydroxy-9-anthrone is followed by thin layer chromatography. After about 2 hours, the reduction reaction is terminated. The 1,8-dihydroxy-10-phenyl-9-anthrone, precipitated in the medium, is filtered, washed with water and dried, yielding 42 g of light yellow crystals. The filtrate is poured over a mixture of 1 liter of water and 1 kg of crushed ice. The remainder of the product which precipitates is filtered, washed with water and dried, yielding an additional 4 g of the expected product.

The 1,8-dihydroxy-10-phenyl-9-anthrone thus obtained is pure and has a melting point of 193°–194° C.

Analysis: $C_{20}H_{14}O_3$; Calculated: C-79.45; H-4.66; O-15.87; Found: C-79.25; H-4.71; O-16.00.

The structure of the 1,8-dihydroxy-10-phenyl-9-anthrone is confirmed by mass spectrography where there is observed on the spectrum the parent peak at m/e: 302 by direct ionization and at m/e: 303 by chemical ionization with isobutane corresponding to M+M+. *These results are in accord with the molar mass of* 302 g of the product.

The NMR spectrum also confirms this structure. There is observed, in particular, a singulet at 5.30 p.p.m. whose integration corresponds to a proton. It is that which is linked to the carbon in the 10-position of the anthrone ring.

The signal of the eleven aromatic protons is a multiplet of which w is from 6.60 to 7.50 p.p.m. (11).

Finally, the spectrum provides another singulet at 12.40 p.p.m., which disappears by exchange with heavy water and the integration of which corresponds indeed to the two protons of the hydroxy groups in positions 1 and 8.

(2) Preparation of 10-phenyl,-1,8,9-triacetoxy-anthracene

A mixture of 40 g of 1,8-dihydroxy-10-phenyl anthrone as obtained in (1) above and 0.5 cm$^3$ of pyridine in 400 cm$^3$ of acetic anhydride is stirred under an inert atmosphere and is progressively brought to a temperature between 60° and 70° C. The initial reactant is quantitatively transformed into the corresponding triacetate at the end of three hours. After cooling on an ice bath, the product crystallizes. It is filtered, washed with ethylether, then dried, 45 g of solid, having a greenish yellow color, are obtianed and are dissolved in a mixture of 200 cm$^3$ of acetic acid and 200 cm$^3$ of 1,2-dichloroethane brought to a temperature of about 80° C. The solution is then filtered at this temperature and on cooling of the filtrate, the product crystallizes. It is filtered, washed with ethyl ether and dried.

35 g of 10-phenyl-1,8,9-triacetoxy anthracene, in the form of light yellow crystals having a melting point of 270° C. are obtained.

Elemental analysis: $C_{26}H_{20}O_6$; Calculated: C-72.86; H-4.70; O-22.40; Found: C-72.87; H-4.73; O-22.15.

EXAMPLE 11

Preparation of 10-phenyl-1,8,9-tripropionyloxy anthracene

To a mixture, stirred under an argon atmosphere, of 2.5 g of 1,8-dihydroxy-10-phenyl anthrone obtained at example 10 (1) in 25 cm$^3$ of propionic anhydride, 0.100 cm$^3$ of anhydrous pyridine is added. The reaction mixture is then brought for one hour to 70° C., at the end of which period all the initial reactant is transformed. The reactive excess is then removed by evaporation under a vacuum. The resulting solid is dissolved in a minimum of toluene, introduced into a silica gel column and then eluted with toluene. After evaporation of the eluant, 1.3 g of a solid are obtained which is then recrystallized in a toluene/hexane mixture, yielding 1.1 g white crystals having a melting point of 216° C.

Elemental analysis: $C_{29}H_{26}O_6$; Calculated: C-74.02; H-5.56; O-20.40; Found: C-74.14; H-5.59; O-20.19.

EXAMPLE 12

Preparation of 10-phenyl-1,8,9-triisobutyryloxy anthracene

A mixture, stirred under an inert atmosphere, of 3 g of 1,8-dihydroxy-10-phenyl anthrone, 3.16 cm$^3$ of pyridine (4 equivalents) in 100 cm$^3$ of anhydrous toluene is brought to the reflux of the solvent for 10 hours. The reaction mixture is then washed several times with water. The organic phase is then decanted, dried on magnesium sulfate and concentrated. The resulting product, in the form of a viscous liquid, is dissolved in a minimum of toluene and introduced into a silica gel column. The expected tri-ester is eluted with a 3/1 toluene/methylene chloride mixture. After concentration of the eluant 2.3 g of a solide are obtained which is then recrystallized in toluene yielding 1.4 g of 10-phenyl-1,8,9-triisobutyryloxy anthracene in the form of yellow crystals having a melting point of 224° C.

Elemental analysis: $C_{32}H_{32}O_6$; Calculated: C-74.98; H-6.29; O-18.72; Found: C-74.98; H-6.27; O-18.57.

EXAMPLE 13

Preparation of 10-phenyl-1,8,9-tri(cyclohexylcarbonyloxy) anthracene

To a mixture of 3 g of 1,8-dihydroxy-10-phenyl anthrone in 15 cm$^3$ of cyclohexane carboxylic acid chloride, there are slowly added, with stirring, 32 cm$^3$ of pyridine. The reaction mixture is then brought for 3 hours at 110° C. It is then diluted at ambient temperature by the addition of 200 cm$^3$ of methylene chloride, washed with bicarbonated water and finally with water. The organic phase is dried on sodium sulfate. After evaporation of the methylene chloride, 4.2 g of a yellow solid are obtained which is then recrystallized in a toluene/ethyl mixture. After filtration and drying 3.75 g of 10-phenyl-1,8,9-tri(cyclohexylcarbonyloxy) anthracene in the form of yellow colored crystals having a melting point of 235° C. are obtained.

Elemental analysis: $C_{41}H_{44}O_6$; Calculated: C-77.82; H-7.00; O-15.17; Found: C-77.97; H-7.00 O-15.01.

EXAMPLE 14

Preparation of 1,8-dipivaloyloxy-10-phenyl-anthrone

A mixture of 3 g of 1,89-dihydroxy-10-phenyl anthrone, 3.16 cm$^3$ of pyridine and 4.8 cm$^3$ of privaloyl chloride in 100 cm$^3$ of anhydrous toluene is stirred under an argon atmosphere for 10 hours at the boiling point of the solvent. After cooling to ambient temperature, the reaction mixture is washed several times with water. The organic phase is decanted, dried on magnesium sulfate and concentrated. The residue, introduced into a silica gel column, is then eluted with toluene. After concentration of the elution phases 2.38 g of a solid are obtained which is recrystallized in a toluene/hexane mixture.

1.4 g of 1,8-dipivaloyloxy-10-phenyl anthrone in the form of white crystals having a melting point of 160° C. are obtained.

Elemental analysis: $C_{30}H_{30}O_5$; Calculated: C-76.57; H-6.42; O-16.99; Found: C-76.40; H-6.40; O-16.92.

EXAMPLE 15

Preparation of 10-phenyl-1,8,9-tribenzoyloxy anthracene

To a mixture, stirred at ambient temperature and under an inert atmosphere, of 1 g of 1,8-dihydroxy-10-phenyl anthrone in 15 cm$^3$ of benzoyl chloride there are slowly added 1.2 cm$^3$ of pyridine.

After stirring for one hour, all of the initial anthrone is transformed into the corresponding tri-ester. The reaction mixture is concentrated under reduced pressure dissolved in 100 cm$^3$ of methylene chloride, washed several times with water and finally dried on sodium sulfate.

The organic phase is then introuduced into a silica gel column and eluted with a toluene/methylene chloride mixture, progressively enriched in methylene chloride.

After concentration of the elution phases, 1.55 g of the expected tri-ester are obtained and the tri-ester is then recrystallized in toluene. The crystals are filtered and dried, yielding 1 g of 10-phenyl-1,8,9-tribenzoyloxy anthracene in the form of yellow crystals having a melting point of 255° C.

Elemental analysis: $C_{41}H_{26}O_6$; Calculated: C-80.12; H-4.26; O-15.62; Found: C-80.08; H-4.32; O-15.79.

EXAMPLE 16

Preparation of 1,8-diisobutyryloxy-10-phenyl-anthrone

A mixture, stirred in the absence of light and under an inert atmosphere, of 18 g of 1,8-dihydroxy-10-phenylanthrone, 19 cm³ of pyridine and 25 cm³ of isobutyryl chloride in 500 cm³ of anhydrous toluene is brought to the reflux of the solvent for 5 hours.

After cooling, the reaction mixture is washed three times with water and dried on magnesium sulfate.

The resulting residue; after evaporation under reduce pressure, is then introduced into a silica gel column. The column is initially eluted with toluene and then with a toluene/methylene chloride mixture, the latter being progressively enriched in methylene chloride.

At the beginning of the chromatography there are isolated, after evaporation of the solvent, 5 g of the 10-phenyl-1,8,9-triisobutyryloxy anthracene described in Example 12.

The following fractions, rich in the diester, are concentrated and the resulting product is recrystallized in a toluene/pentane mixture.

1.5 g of 1,8-diisobutyryloxy-10-phenyl anthrone in the form of beige crystals having a melting point of 136° C. are obtained.

Elemental analysis: $C_{28}H_{26}O5$; Calculated: C-76.00; H-5.92; O-18.08; Found: C-75.75; H-5.99; O-18.36.

EXAMPLE 17

Preparation of 10-(3'-methoxy phenyl)-1,8,9-triacetoxy anthracene

In a three-necked flask equipped with a magnetic agitator and a nitrogen lead in tube there are stirred 200 mg of 10-(3'-methoxy phenyl)-1,8 anthrone obtained in accordance with the procedures outlined in example 5, in 5 cm³ of acetic anydride and several drops of pyridine. The mixture is stirred at 80° C. for 3 hours and then cooled. The expected triester crystallizes after which it is filtered and then washed with hexane, yielding 150 mg of light yellow crystals having a melting point of 278° C.

Elemental analysis: $C_{27}H_{22}O_7$; Calculated: C 70.73; H 4.84; O 24.43; Found: C 70.47; H 5.01; O 24.24.

EXAMPLE 18

Preparation of 10-(3'methoxy phenyl)-1,8,9-tripropanoyloxy anthracene

In a three-necked flask equipped with a magnetic agitator, there are stirred 250 mg of 10-(3'-methoxy phenyl)-1,8-dihydroxy anthrone, obtained according to example 5, in 5 cm³ of propionic anhydride and several drops of pyridine. The resulting mixture is stirred at 80° C. for 6 hours under an inert atmosphere.

The solution is poured into 100 cm³ of water, extracted with ether, then washed with an aqueous solution of sodium bicarbonate. It is then dried on magnesium sulfate and concentrated under reduced pressure. Addition of hexane yields 200 mg of the expected triester.

The resulting yellow crystals have a melting point of 177°–178° C. The NMR spectrum and the mass spectrum (m/e: 500) correspond to the structure of the expected product.

EXAMPLE 19

Preparation of 10-(2-thienyl)-1,8,9-triacetoxy anthracene

In a three-necked flask equipped with a magnetic agitator, there are stirred 250 mg of 10-(2-thienyl)-1,8-dihydroxy anthrone, obtained according to example 8, in 5 cm³ of acetic anhydride and several drops of pyridine. The mixture is stirred for 3 hours at 80° C. under an inert atmosphere, then cooled. The expected triester crystallizes and is then filtered and washed with hexane, yielding 300 mg of light yellow crystals having a melting point of 260° C.

Elemental analysis: $C_{24}H_{18}O_6S$; Calculated: C 66.35; H 4.17; O 22.10; 7.38; Found: C 66.35; H 4.19; O 22.20; 7.26.

EXAMPLE 20

Preparation of 10-(2-thienyl)-1,8,9-tripropanoyloxy anthracene

In a three-necked flask equipped with a magnetic agitator, there are stirred 250 mg of 10-(2-thienyl)-1,8-dihydroxy anthrone, obtained according to example 8, in 5 cm³ of propionic anhydride and several drops of pyridine. The mixture is stirred for 6 hours at 80° C. under a nitrogen atmosphere. On cooling, the expected product precipitates, 120 mg of yellow crystals are isolated. The filtrate is poured into 100 cm³ of water, extracted with ether, and washed with an aqueous solution of sodium bicarbonate. The ether phase is then dried and concentrated under reduce pressure. On addition of hexane to the residue, there are obtained 130 additional mgs of the expected triester. The light yellow crystals have a melting point of 192° C. The NMR spectrum and the mass spectrum (m/e: 476) correspond to the structure of the expected product.

EXAMPLE 21

Preparation of 1,8-dipivaloyloxy-10-(2 thienyl) anthrone

To a solution, stirred at room temperature in the absence of light and atmospheric humidity, of 2 g of 10-(2-thienyl)1,8-dihydroxy anthrone obtained according to example 8 in 150 cm³ of anhydrous toluene, there are added five equivalents of pyridine and immediately thereafter with five molar equivalents of pivaloyl chloride. the reaction mixture is refluxed for eight hours, after which time the starting product is transformed.

The reaction mixture is then concentrated under reduced pressure, taken up with water, and extracted with methylene chloride.

The methylene chloride phase is washed with water, decanted, dried on magnesium sulfate, and concentrated.

The resulting solid is recrystallized in a hexane-ethylacetate yielding 1.5 g of yellow crystals that melt at 170° C.

The NMR spectrum and the mass spectrum (m/e: 476) correspond to the structure of expected product.

PHARMACEUTICAL AND COSMETIC COMPOSITIONS

EXAMPLE 1

0.5 g powder capsules

Into capsules made of gelatin, titanium dioxide and a preservative, there is packaged 0.5 g of the following powder:

| | |
|---|---|
| 1,8-dimethoxy-10-(2'-methoxy phenyl) anthrone | 0.3 g |
| Potato flour | 0.1 g |
| Lactose, sufficient amount for | 0.5 g |

EXAMPLE 2

Tablets weighing 1 g are made by mixing the following components:

| | |
|---|---|
| 1,8-dihydroxy-10-(2-thienyl) anthrone | 0.4 g |
| Polyvinyl pyrrolidone | 0.013 g |
| Cross-linked polyvinyl pyrrolidone | 0.05 g |
| Talc | 0.08 g |
| "Aerosil 200" silica sold by Degussa | 0.001 g |
| Lactose, sufficient amount for | 100 g |

In this example, the 1,8-dihydroxy-10-(2-thienyl) anthrone can be replaced with an equivalent quantity of 1,8-dihydroxy-10-(3'-methoxy phenyl) anthrone.

EXAMPLE 3

Composition in syrup form

At the time of use, there are mixed with stirring in 60 ml of mineral water, 30 g of a powder having the following composition:

| | |
|---|---|
| 1,8-dihydroxy-10-(3'-hydroxy phenyl) anthrone | 0.6 g |
| Sodium benzoate | 0.15 g |
| Sodium chloride | 0.23 g |
| Anhydrous sodium citrate | 1.1 g |
| Ammonium glycyrrhizinate | 0.06 g |
| Fragance, a sufficient quantity | |
| Coloring agent, a sufficient quantity | |
| Sucrose, in an amount sufficient for | 30 g |

Once made up, the syrup should be kept cool, since its stability does not exceed 7 days.

EXAMPLE 4

Hydrophobic anhydrous gel

| | |
|---|---|
| 1,8-dihydroxy-10-(3'-hydroxy phenyl) anthrone | 1 g |
| "Aerosil 200", silica sold by Degussa | 7 g |
| Isopropyl myristate, sufficient amount for | 100 g |

EXAMPLE 5

Occlusive hydrophobic ointment

| | |
|---|---|
| 1,8-dihydroxy-10-(2'-methoxy phenyl) anthrone | 1.6 g |
| Ceresin | 15 g |
| Petrolatum oil | 35 g |
| Petrolatum, sufficient amount for | 100 g |

In this example, the 1,8-dihydroxy-10-(2'-methoxy phenyl) anthrone can be replaced with an equivalent quantity of 1,8-dihydroxy-10-(3'-methoxy-phenyl) anthrone.

EXAMPLE 6

Hydrophobic ointment in paste form

| | |
|---|---|
| 1,8-dihydroxy-10-(2-thienyl) anthrone | 1.5 g |
| Isopropyl myristate | 36.4 g |
| Silicone oil (dimethyl polysiloxane, sold by Rhone Poulenc under trade name "Rhodorsil 47 V 300") | 36.4 g |
| Beeswax | 13.6 g |
| Silicone oil, sold by Goldschmidt under the trade name "Abil 300 000 cst", sufficient amount for | 100 g |

EXAMPLE 7

A two-part shampoo composition to be admixed at the time of use

| | |
|---|---|
| (1) Conditioning part, (in suspension form) | |
| 1,8-dihydroxy-10-(3'-methoxy phenyl) anthrone | 0.5 g |
| Petrolatum oil, sufficient amount for | 100 g |
| (2) Washing part | |
| Docecane diol polyglycerolated with 3.5 moles of glycerol | 20 g |
| Compound of the formula | 1.75 g |

$$HO(CH-CH_2O)_x(CH_2-CH_2-O)_n(CH_2-CH)_yH$$
$$\phantom{HO(CH}|\phantom{CH_2O)_x(CH_2-CH_2-O)_n(CH_2-CH)_yH}$$
$$\phantom{HO(CH}R$$

$R = C_{14}H_{29}$, $x + y = 3$ et $n \simeq 70$

| | |
|---|---|
| Water sufficient amount for | 100 g |

After vigorously stirring the conditioning part, it is admixed in an applicator bottle with the washing part in a ratio of 10:90. Once mixed, the product must be used immediately.

EXAMPLE 8

Anti-acne composition in creme form

| | |
|---|---|
| Magnesium lanolate | 3.4 g |
| Lanolin alcohol | 2.8 g |
| Perhydrosqualene | 20 g |
| Isopropyl myristrate | 5 g |
| Virgin sesame oil | 10 g |
| Petrolatum | 8.8 g |
| Salicylic acid | 1 g |
| 10-(2-thienyl)-1,8,9-tripropanoyloxy anthracene | 1 g |
| Methyl parahydroxybenzoate | 0.3 g |
| Water, sufficient amount for | 100 g |

EXAMPLE 9

Composition to combat hair loss and dandruff

| | |
|---|---|
| 10-(3'-methoxy phenyl)-1,8,9-triacetoxy anthracene | 0.5 g |
| Salicylic acid | 0.1 g |
| Benzyl salicylate, sufficient amount for | 100 g |

EXAMPLE 10

Composition to combat hair loss and dandruff

| | |
|---|---|
| 1,8-dipivaloyloxy-10-(2-thienyl) anthrone | 0.8 g |
| Stannous chloride | 0.3 g |
| Isopropyl myristate, sufficient amount for | 100 g |

EXAMPLE 11

Anti-seborrheic lotion

To a solution of 10 cm$^3$ of 95° ethanol and 30 cm$^3$ of polyethylene glycol (PEG) 400 containing 20 mg of butylhydroxy-toluene, there is added 0.2 g of 1,8-dipivaloyloxy-10-(2-thienyl) anthrone.

After solubilizing the product by stirring, the lotion is applied to the hair.

Preferably this treatment should be carried out twice daily.

EXAMPLE 12

0.5 g non-soluble compressed tablet

| | |
|---|---|
| 10-phenyl-1,8,9-triacetoxy anthracene | 0.100 g |
| Lactose | 0.082 g |
| Stearic acid | 0.003 g |
| Purified talc | 0.015 g |
| Sweetening agent, sufficient amount | |
| Rice starch, sufficient amount for | 0.500 g |

This compressed tablet is prepared by directly dry compressing the mixture of the various components thereof.

EXAMPLE 13

0.8 g non-soluble compressed tablet

| | |
|---|---|
| 10-phenyl-1,8,9-triisobutyryloxy anthracene | 0.200 g |
| Lactose | 0.200 g |
| Gum arabic, 20% in water | 0.080 g |
| Liquid paraffin | 0.004 g |
| Purified talc | 0.016 g |
| Starch, sufficient amount for | 0.800 g |

This compressed tablet is obtained by wet granulation of the mixture of 10-phenyl-1,8,9-triisobutyryloxy anthracene, starch, lactose and gum arabic (20% in water).

The resulting granules are dried and then screened. The screened granules are then admixed with the paraffin and talc.

EXAMPLE 14

Granules in 3 g sachets

| | |
|---|---|
| 10-phenyl-1,8,9-tripropionyloxy anthracene | 0.150 g |
| Sucrose | 2.220 g |
| Methyl cellulose | 0.030 g |
| Purified water | 0.600 g |

The paste obtained by the mixture of the above four components is wet granulated and then dried.

EXAMPLE 15

Capsules containing 0.05 g of active compound

| | |
|---|---|
| 10-phenyl-1,8,9-tricyclohexylcarbonyloxy anthracene | 0.050 g |
| Cod liver oil, sufficient amount for | 0.500 g |

The envelope of the capsule is manufactured by grinding and then drying, an appropriate mixture of gelatin, glycerine, water and preservative. The suspension containing the active compound is introduced into the capsule which is then sealed.

EXAMPLE 16

Gelule containing 0.3 g of powder

| | |
|---|---|
| 1,8-dipivaloyloxy-10-phenyl anthrone | 0.080 g |
| Cornstarch | 0.060 g |
| Lactose, sufficient amount for | 0.300 g |

The powder is packaged in a gelule composed of gelatin, titanium dioxide and a preservative.

EXAMPLE 17

Hydrophobic ointment

| | |
|---|---|
| 1,8-dipivaloyloxy-10-phenyl anthrone | 1.00 g |
| Petrolatum | 49.00 g |
| Ceresin | 15.00 g |
| Salicylic acid | 0.30 g |
| Petrolatum | 34.70 g |

EXAMPLE 18

Non-ionic emulsion for topical application

| | |
|---|---|
| 10-phenyl-1,8,9-triacetoxy anthracene | 0.70 g |
| Anhydrous eucerine | 70.00 g |
| Petrolatum oil | 10.00 g |
| Butylhydroxytoluene, sufficient amount | |
| Sterile demineralized water, sufficient amount for | 100.00 g |

For good preservation, this emulsion should be stored in the absence of heat and light.

EXAMPLE 19

Anhydrous gel

| | |
|---|---|
| 1,8-dipivaloyloxy-10-phenyl anthrone | 1.50 g |
| "Aerosil 200" (silica) sold by Degussa | 7.00 g |
| Isopropyl myristate, sufficient amount for | 100.00 g |

EXAMPLE 20

Two part milk to be emulsified at the time of use

| | |
|---|---|
| 10-phenyl-1,8,-tripropionyloxy anthracene | 2.00 g |
| "Miglyol 812" (triglycerides of capric/caprylic acids) sold by Dynamit Nobel, sufficient amount for | 20.00 g |
| "Tween 80" (sorbitan mono-oleate polyoxyethylenated with 20 moles of ethylene oxide), sold by Atlas | 10.00 g |
| Preservatives, sufficient amount | |
| Sterile demineralized water, sufficient amount for | 80.00 g |

The first part is stirred so as to suspend the active compound therein. The two parts are then mixed together before applying the milk.

EXAMPLE 21

Stick

| 10-phenyl-1,8,9-triisobutyryloxy anthracene | 5.00 g |
|---|---|
| Cocoa butter | 12.50 g |
| Ozokerite wax | 18.50 g |
| Refined white paraffin | 6.25 g |
| Petroleum oil | 12.75 g |
| Isopropyl myristate, sufficient amount for | 100.00 g |

EXAMPLE 22

Anti-hair loss and anti-pellicular capillary composition

| 1,8-dipivaloyloxy-10-phenyl anthrone | 0.50 g |
|---|---|
| Stannous chloride | 0.30 g |
| Isopropyl myristate, sufficient amount for | 100.00 g |

EXAMPLE 23

Ointment

| 1,8-diisobutyryloxy-10-phenyl anthrone | 1.00 g |
|---|---|
| "Miglyol 812" (triglycerides of capric/capyrlic acids) sold by Dynamit Nobel | 49.25 g |
| White petrolatum | 49.25 g |
| Salicylic acid | 0.50 g |

What is claimed is:

1. A 10-aryl-1,8-dihydroxy anthrone having the formula

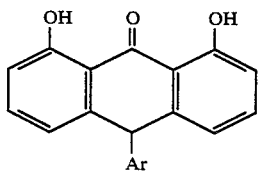

(I)

wherein
Ar represents an aromatic radical having a formula selected from

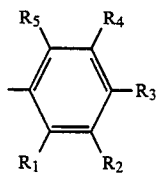

(i)

wherein
$R_1$, $R_2$, $R_3$, $R_4$ and $R_5$, each independently, represent hydrogen, halogen, —$CF_3$, hydroxyl, lower alkyl, lower cycloalkyl, lower hydroxyalkyl, lower alkoxy, nitrile,

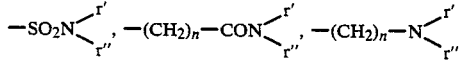

wherein r' and r", each independently, represent hydrogen or lower alkyl, n equals 0 or a whole number ranging from 1 to 3 inclusive; R' and R" represent hydrogen, linear or branched lower alkyl, or aryl, with the proviso that at least one of $R_1$–$R_5$ is

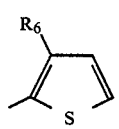

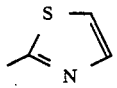
(ii)

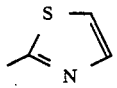
(iii)

wherein $R_6$ represents one of the meanings given for $R_1$–$R_5$ and,

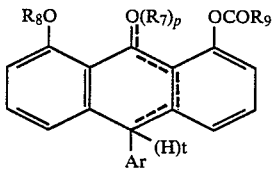
(iv)

2. The mono-, di-, and triesters of 10-aryl-1,8-dihydroxy-9-anthrone having the formula (II)

wherein
p is 0 or 1,
 (a) when p equals 0, t equals 1 and $R_8$ represents hydrogen or —$COR_9$,
 (b) when p equals 1, t equals 0 and $R_7$ and $R_8$, each independently, represent hydrogen or —$COR_9$,
$R_9$ represents linear of branched alkyl having 1–17 carbon atoms, cycloalkyl, phenyl, phenyl substituted by lower alkyl, lower alkoxy, halogen, nitro, —$CF_3$ or hydroxyl, and
Ar represents an aromatic radical having one of the following formulas:

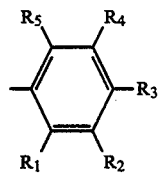 (i)

wherein $R_1$, $R_2$, $R_3$, $R_4$ and $R_5$, each independently, represent hydrogen, halogen, —$CF_3$, hydroxy, lower alkyl, lower cycloalkyl, lower hydroxyalkyl, lower alkoxy, nitrile,

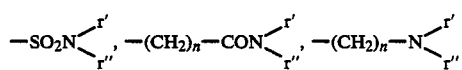

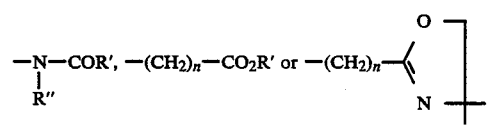

wherein r' and r'', each independently, represent hydrogen or lower alkyl; n is 0 or a whole number from 1 to 3 inclusive; and R' and R'' represent hydrogen, linear or branched lower alkyl, or aryl, with the proviso that at least one of $R_1$–$R_5$ is

 (ii)

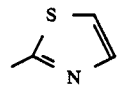 (iii)

wherein $R_6$ represents one of the meanings given for $R_1$–$R_5$ and (iv)

3. A pharmaceutical or cosmetic composition comprising in a pharmaceutically or cosmetically acceptable carrier from 0.01 to 5 percent by weight, based on the total weight of said composition, of an anthrone of claim 1 or a mono-, di- and/or triester of claim 2.

* * * * *

UNITED STATES PATENT AND TRADEMARK OFFICE
CERTIFICATE OF CORRECTION

PATENT NO. : 4,889,865

DATED : December 26, 1989

INVENTOR(S) : SHROOT et al

It is certified that error appears in the above-identified patent and that said Letters Patent is hereby corrected as shown below:

On the title page item [73] insert

Assignee: -- Groupement d'Interet Economique dit: CENTRE INTERNATIONAL DE RECHERCHES DERMATOLOGIQUES, C.I.R.D., Valbonne, France --

The Attorney, Agent, or Firm should read

--Cushman, Darby & Cushman--.

Signed and Sealed this

Twenty-seventh Day of September, 1994

Attest:

BRUCE LEHMAN

*Attesting Officer*     *Commissioner of Patents and Trademarks*